(12) United States Patent
Kottenstette et al.

(10) Patent No.: US 11,918,423 B2
(45) Date of Patent: Mar. 5, 2024

(54) SYSTEM AND METHOD FOR NAVIGATING A DEVICE THROUGH A PATH TO A TARGET LOCATION

(71) Applicant: Corindus, Inc., Waltham, MA (US)

(72) Inventors: Nicholas Kottenstette, Worcester, MA (US); Per Bergman, West Roxbury, MA (US); Steven J. Blacker, Framingham, MA (US); Adi Dafni, Giva'at Brener (IL); Adi Sheinfeld, Durham, NC (US)

(73) Assignee: Corindus, Inc., Newton, MA (US)

( * ) Notice: Subject to any disclaimer, the term of this patent is extended or adjusted under 35 U.S.C. 154(b) by 1192 days.

(21) Appl. No.: 16/175,333

(22) Filed: Oct. 30, 2018

(65) Prior Publication Data

US 2020/0129740 A1 Apr. 30, 2020

(51) Int. Cl.
*A61B 90/00* (2016.01)
*A61M 25/09* (2006.01)
(Continued)

(52) U.S. Cl.
CPC ............. *A61B 90/37* (2016.02); *A61M 25/09* (2013.01); *G06T 7/0012* (2013.01); *G06V 10/25* (2022.01); *A61M 2025/0166* (2013.01); *A61M 2025/09166* (2013.01); *A61M 2025/09183* (2013.01); *G06T 2207/10064* (2013.01)

(58) Field of Classification Search
CPC .......... A61M 25/09; A61M 2025/0166; G06T 7/0012; G06V 10/25
See application file for complete search history.

(56) References Cited

U.S. PATENT DOCUMENTS 7,697,972 B2 4/2010 Verard et al.
7,831,292 B2 11/2010 Quaid et al.
(Continued)

FOREIGN PATENT DOCUMENTS

CN 102028549 B 6/2012
CN 111243746 A 6/2020
(Continued)

OTHER PUBLICATIONS

Azizian M et al: "Image processing algorithms for real-time tracking and control of an active catheter", 2007 European Control Conference (ECC), IEEE, [Online] Jul. 2, 2007 (Jul. 2, 2007), pp. 2135-2142, XP032751967, ISBN: 978-3-9524173-8-6 https://ieeexplore.ieee.org/document/7068828 [retrieved on Mar. 25, 2015].

(Continued)

*Primary Examiner* — Rochelle D Turchen

(57) ABSTRACT

A method for delivering an elongated medical device along a path to a target location using a catheter procedure system includes generating a mask of the path, tracking a position of a distal portion of the elongated medical device based on a set of real-time images and determining a remaining path length based at least on the position of the distal portion of the elongated medical device. The remaining path length is a distance between the distal portion of the elongated medical device and the target location. The remaining path length decreases as the distal portion of the elongated medical device approaches the target location.

46 Claims, 12 Drawing Sheets

(51) Int. Cl.
*G06T 7/00* (2017.01)
*G06V 10/25* (2022.01)
*A61M 25/01* (2006.01)

(56) References Cited

U.S. PATENT DOCUMENTS

| | | | |
|---|---|---|---|
| 8,005,283 B2 | 8/2011 | John et al. |
| 8,050,739 B2 | 11/2011 | Eck et al. |
| 8,229,186 B2 | 7/2012 | Milstein et al. |
| 8,275,448 B2 | 9/2012 | Camus et al. |
| 8,346,344 B2 | 1/2013 | Pfister et al. |
| 8,542,900 B2 | 9/2013 | Tolkowsky et al. |
| 8,632,468 B2 | 1/2014 | Glossop et al. |
| 8,634,896 B2 | 1/2014 | Sra et al. |
| 8,795,188 B2 | 8/2014 | Maschke |
| 8,936,596 B2 | 1/2015 | Mittelstadt et al. |
| 9,014,781 B2 | 4/2015 | Tan et al. |
| 9,024,941 B2 | 5/2015 | Itai |
| 9,095,308 B2 | 8/2015 | Florent et al. |
| 9,218,664 B2 | 12/2015 | Edwards et al. |
| 9,259,290 B2 | 2/2016 | Jenkins et al. |
| 9,629,570 B2 | 4/2017 | Bar-Tal |
| 9,661,991 B2 | 5/2017 | Glossop |
| 9,675,272 B2 | 6/2017 | Selover et al. |
| 9,775,538 B2 | 10/2017 | Eichler |
| 9,811,939 B2 | 11/2017 | Aben et al. |
| 9,888,864 B2 | 2/2018 | Rondoni et al. |
| 10,603,124 B2 | 3/2020 | Camarillo et al. |
| 2001/0031919 A1 | 10/2001 | Strommer et al. |
| 2005/0251030 A1* | 11/2005 | Azar ............... A61B 90/36 600/429 |
| 2009/0326324 A1 | 12/2009 | Martinez et al. |
| 2010/0161023 A1 | 6/2010 | Cohen et al. |
| 2011/0160570 A1* | 6/2011 | Kariv ............... A61B 6/12 600/424 |
| 2012/0063644 A1 | 3/2012 | Popovic |
| 2012/0089008 A1 | 4/2012 | Strehl et al. |
| 2012/0257807 A1 | 10/2012 | Sapp et al. |
| 2013/0158346 A1* | 6/2013 | Soper ............... A61B 1/00045 600/110 |
| 2014/0275982 A1 | 9/2014 | Hendrick et al. |
| 2015/0282890 A1* | 10/2015 | Cohen ............... A61B 5/1128 600/424 |
| 2015/0351860 A1 | 12/2015 | Piron et al. |
| 2016/0007827 A1 | 1/2016 | Frimer et al. |
| 2016/0022484 A1 | 1/2016 | Yu et al. |
| 2016/0067448 A1 | 3/2016 | Blacker |
| 2016/0317233 A1 | 11/2016 | Hunter et al. |
| 2017/0007327 A1 | 1/2017 | Haider et al. |
| 2017/0202624 A1* | 7/2017 | Atarot ............... A61B 90/03 |
| 2017/0245942 A1 | 8/2017 | Penenberg et al. |
| 2017/0265943 A1 | 9/2017 | Sela et al. |
| 2017/0311908 A1 | 11/2017 | Kariv et al. |
| 2017/0360372 A1 | 12/2017 | Hauck et al. |
| 2018/0085173 A1 | 3/2018 | Dickhans |
| 2018/0276823 A1* | 9/2018 | Barral ............... A61B 5/7207 |
| 2018/0336676 A1* | 11/2018 | Dutta ............... G06T 7/187 |

FOREIGN PATENT DOCUMENTS

| | | |
|---|---|---|
| EP | 2612606 B1 | 10/2015 |
| JP | 2004505748 | 2/2004 |
| JP | 2007190288 A | 8/2007 |
| JP | 2012213426 A | 11/2012 |
| WO | 2017098506 | 7/2017 |
| WO | 2018175339 | 9/2018 |

OTHER PUBLICATIONS

European Search Report Rec'd for Corresponding Application No. EP 19880029.4, dated Jul. 13, 2022.

* cited by examiner

SYSTEM AND METHOD FOR NAVIGATING A DEVICE THROUGH A PATH TO A TARGET LOCATION

FIELD

The present invention relates generally to the field of catheter procedure systems and, in particular, a system and method for navigating a device (e.g., an elongated medical device) through a path (e.g., a vessel) to a target location.

BACKGROUND

Catheters (and other elongated medical devices) may be used for many minimally-invasive medical procedures for the diagnosis and treatment of diseases of various vascular systems, including neurovascular interventional (NVI) also known as neurointerventional surgery, percutaneous coronary intervention (PCI) and peripheral vascular intervention (PVI). These procedures typically involve navigating a guidewire through the vasculature, and via the guidewire advancing a working catheter to deliver therapy. The catheterization procedure starts by gaining access into the appropriate vessel, such as an artery or vein, with a sheath or guide catheter using standard percutaneous techniques. The sheath or guide catheter is then advanced over a diagnostic guidewire to the primary location such as an internal carotid artery for NVI, a coronary ostium for PCI or a superficial femoral artery for PVI. A guidewire suitable for the vasculature is then navigated through the sheath or guide catheter to a target location in the vasculature. In certain situations, such as in tortuous anatomy, a support catheter or microcatheter is inserted over the guidewire to assist in navigating the guidewire. The physician or operator may use an imaging system (e.g., fluoroscope) to obtain a cine with a contrast injection and select a fixed frame for use as a roadmap to navigate the guidewire or catheter to the target location, for example a lesion. Contrast-enhanced images are also obtained while the physician delivers the guidewire or catheter device so that the physician can verify that the device is moving along the correct path to the target location. While observing the anatomy using fluoroscopy, the physician manipulates the proximal end of the guidewire or catheter to direct the distal tip into the appropriate vessels toward the lesion and avoid advancing into side branches.

Robotic catheter procedure systems have been developed that may be used to aid a physician in performing catheterization procedures such as, for example, NVI, PCI and PVI. Examples of neurovascular intervention (NVI) catheter procedures include coil embolization of aneurysms, liquid embolization of arteriovenous malformations and mechanical thrombectomy of large vessel occlusions in the setting of acute ischemic stroke. In NVI, the physician uses a robotic system to gain lesion access by manipulating a neurovascular guidewire and microcatheter to deliver the therapy to restore normal blood flow. The access is enabled by the sheath or guide catheter but may also require an intermediate catheter for more distal territory or to provide adequate support for the microcatheter and guidewire. The distal tip of a guidewire is navigated into, or past, the lesion depending on the type of lesion and treatment. For treating aneurysms, the microcatheter is advanced into the lesion and the guidewire is removed and several coils are deployed into the aneurysm through the microcatheter and used to embolize the aneurysm. For treating arteriovenous malformations, a liquid embolic is injected into the malformation via a microcatheter. Mechanical thrombectomy to treat vessel occlusions can be achieved either through aspiration or use of a stent retriever. Aspiration is either done directly through the microcatheter, or with a larger bore aspiration catheter. Once the aspiration catheter is at the lesion, negative pressure is applied to remove the clot through the catheter. Alternatively, the clot can be removed by deploying a stent retriever through the microcatheter. Once the clot has integrated into the stent retriever, the clot is retrieved by retracting the stent retriever and microcatheter into the guide catheter.

In PCI, the physician uses a robotic system to gain lesion access by manipulating a coronary guidewire to deliver the therapy and restore normal blood flow. The access is enabled by seating a guide catheter in a coronary ostium. The distal tip of the guidewire is navigated past the lesion and, for complex anatomies, a microcatheter may be used to provide adequate support for the guidewire. The blood flow is restored by delivering and deploying a stent or balloon at the lesion. The lesion may need preparation prior to stenting, by either delivering a balloon for pre-dilation of the lesion, or by performing atherectomy using, for example, a laser or rotational atherectomy catheter and a balloon over the guidewire. Diagnostic imaging and physiological measurements may be performed to determine appropriate therapy by using imaging catheters or FFR measurements.

In PVI, the physician uses a robotic system to deliver the therapy and restore blood flow with techniques similar to NVI and PVI. The distal tip of the guidewire is navigated past the lesion and a microcatheter may be used to provide adequate support for the guidewire for complex anatomies. The blood flow is restored by delivering and deploying a stent or balloon to the lesion. As with PCI, lesion preparation and diagnostic imaging may be used as well.

There are several challenges presented when performing a catheter procedure either manually or with a robotic catheter procedure system. For example, the path traversed by a device through the vasculature may change during a physiological cycle such as a heart or respiratory cycle which can lengthen the amount of time required to successfully navigate the device. In addition, the amount of contrast used during navigation of a device may adversely affect the patient (e.g., if there is more than one lesion requiring treatment). It would be desirable to provide a system and method for navigating a device (e.g., an elongated medical device) through a path (e.g., a vessel) to a target location that reduces the procedure time and reduces the amount of contrast agent used during the procedure.

SUMMARY

In accordance with an embodiment, a method for delivering an elongated medical device along a path to a target location using a catheter procedure system includes generating a mask of the path, tracking a position of a distal portion of the elongated medical device based on a set of real-time images, determining a remaining path length based at least on the position of the distal portion of the elongated medical device, the remaining path length being a distance between the distal portion of the elongated medical device and the target location, wherein the remaining path length decreases as the distal portion of the elongated medical device approaches the target location, updating the remaining path length during movement of the elongated medical device, determining if the distal portion of the elongated medical device is off path, adjusting the position of the elongated medical device if the distal portion of the elongated medical device is off path, and advancing the elongated medical device to the target location at a velocity determined based at least on the remaining path length.

In accordance with another embodiment, a system for delivering an elongated medical device along a path to a target location includes an imaging system and a catheter procedure system coupled to the imaging system. The catheter procedure system includes a bedside system comprising an elongated medical device and a drive assembly configured to drive the elongated medical device and a workstation coupled to the bedside system. The workstation includes a user interface and a controller coupled to the bedside system, the user interface and the imaging system. The controller is programmed to generate a mask of the path, track the position of a distal portion of the elongated medical device based on a set of real-time images acquired by the imaging system, determine a remaining path length based at least on the position of the distal portion of the elongated medical device, the remaining path length being a distance between the distal portion of the elongated medical device and the target location, wherein the remaining path length decreases as the distal portion of the elongated medical device approaches the target location, update the remaining path length during movement of the elongated medical device, determine if the distal portion of the elongated medical device is off path, adjust the position of the distal portion of the elongated medical device if the distal portion of the elongated medical device is off path, and advance the elongated medical device to the target location at a velocity determined based at least on the remaining path length using the drive assembly.

In accordance with another embodiment a method for generating a mask of a calculated path to a target location and tracking a position of an elongated medical device moving along the path, the method includes acquiring a set of contrast-enhanced images of a region of interest, generating a vessels-image based on at least one image from the set of contrast-enhanced images, identifying a source point and a target point on the vessels-image, calculating a vessel path from the source point to the target point based at least on the set of contrast-enhanced images, generating a path mask for the vessel path, determining if at least one child vessel is connected to the vessel path based on at least a flow of contrast agent in the set of contrast-enhanced images, and if at least one child vessel is connected to the path, generating a child vessel mask for the at least one child vessel, applying and displaying the path mask on an image associated with the path mask and if at least one child vessel is determined to be connected to the vessel path, and applying and displaying the child vessel mask for the at least one child vessel on the image associated with the path mask.

In accordance with another embodiment, a system for generating a mask of a calculated path to a target location and tracking a position of an elongated medical device moving along the path, the system includes an imaging system. A workstation os coupled to the imaging system, the workstation includes a user interface, at least one display; and a controller coupled to the user interface, the at least one display and the imaging system. The controller is programmed to receive a set of contrast-enhanced images of a region of interest from the imaging system, generate a vessels-image based on at least one image from the set of contrast-enhanced images, receive an identification of a source point and a target point on the vessels-image, calculate a vessel path from the source point to the target point based at least on the set of contrast-enhanced images, determine if at least one child vessel is connected to the vessel path based on at least a flow of contrast agent in the set of contrast-enhanced images, generate a path mask for the vessel path. If at least one child vessel is connected to the vessel path, generate a child vessel mask for the at least one child vessel; and display the path mask on an image associated with the path mask on the display and if at least one child vessel is connected to the vessel path, display the child vessel mask for the at least one child vessel on the image associated with the path mask on the display

BRIEF DESCRIPTION OF THE DRAWINGS

The invention will become more fully understood from the following detailed description, taken in conjunction with the accompanying drawings, wherein the reference numerals refer to like parts in which.

DETAILED DESCRIPTION

Figure 1:
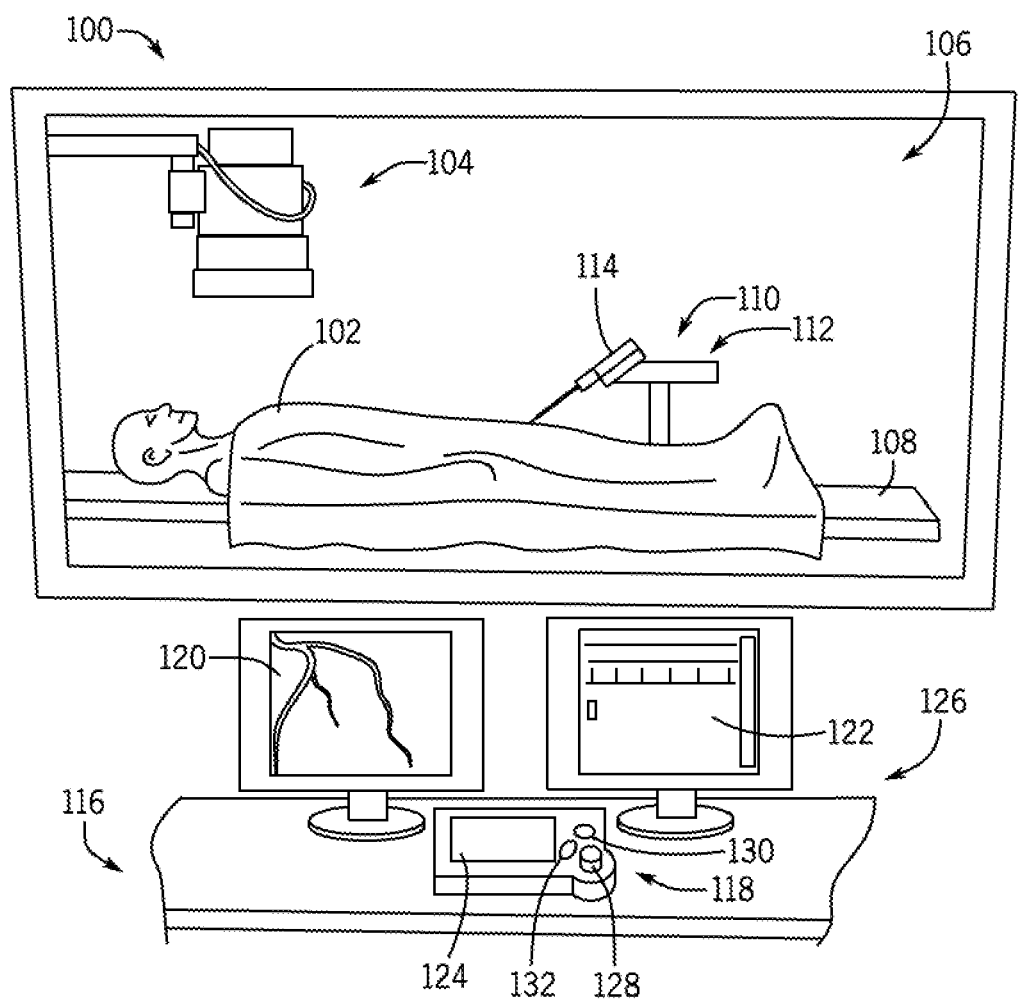
FIG. 1 is a perspective view of an exemplary catheter procedure system in accordance with an embodiment.

FIG. 1 is a perspective view of an exemplary catheter procedure system in accordance with an embodiment. In FIG. 1, a catheter procedure system 100 may be used to perform catheter based medical procedures (e.g., neurovascular interventional (NVI), percutaneous intervention (PCI), peripheral vascular intervention (PVI)). Catheter based medical procedures may include diagnostic catheterization procedures during which one or more catheters are used to aid in the diagnosis of a patient's disease. For example, during one embodiment of a catheter based diagnostic procedure, a contrast media is injected onto one or more coronary arteries through a catheter and an image of the patient's heart is taken. Catheter based medical procedures may also include catheter based therapeutic procedures (e.g., angioplasty, stent placement, treatment of peripheral vascular disease, clot removal, arterial venous malformation therapy, treatment of aneurysm, etc.) during which a catheter is used to treat a disease. It should be noted, however, that one skilled in the art would recognize that certain specific percutaneous intervention devices or components (e.g., type of guidewire, type of catheter, etc.) will be selected based on the type of procedure that is to be performed. Catheter procedure system 100 is capable of performing any number of catheter based medical procedures with minor adjustments to accommodate the specific percutaneous intervention devices to be used in the procedure. In particular, while the embodiments of catheter procedure system 100 described herein are explained primarily in relation to the diagnosis and/or treatment of coronary disease, catheter procedure system 100 may be used to diagnose and/or treat any type of disease or condition amenable to diagnosis and/or treatment via a catheter-based procedure.

Catheter procedure system 100 includes lab unit 106 and workstation 116. Catheter procedure system 100 includes a robotic catheter system, shown as bedside system 110, located within lab unit 106 adjacent a patient 102. Patient 102 is supported on a table 108. Generally, bedside system 110 may be equipped with the appropriate percutaneous intervention devices or other components (e.g., guidewires, guide catheters, microcatheters, embolization coils, working catheters such as balloon catheters, stent delivery systems, aspiration catheters and atherectomy catheters, contrast media, medicine, diagnostic catheters, etc.) to allow the user to perform a catheter based medical procedure via a robotic system by operating various controls such as the controls located at workstation 116. Bedside system 110 may include any number and/or combination of components to provide bedside system 110 with the functionality described herein. Bedside system 110 includes, among other elements, a drive assembly 114 (e.g., a cassette) supported by a robotic arm 112 which is used to feed a guidewire into a guide catheter seated in an artery of the patient 102 or to feed other elongated medical devices (e.g., catheters, balloon catheters, stent delivery systems, etc.) into the patient 102.

Bedside system 110 is in communication with workstation 116, allowing signals generated by the user inputs of workstation 116 to be transmitted to bedside system 110 to control the various functions of bedside system 110. Bedside system 110 may also provide feedback signals (e.g., operating conditions, warning signals, error codes, etc.) to workstation 116. Bedside system 110 may be connected to workstation 116 via a communication link 140 (shown in FIG. 2) that may be a wireless connection, cable connections, or any other means capable of allowing communication to occur between workstation 116 and bedside system 110. In an embodiment, the bedside system 110 and workstation 116 are remote from one another, for example, different rooms in the same building, different buildings in the same city or different cities. In another embodiment, a plurality of workstations 116 may be connected to the bedside system 110 and located remotely from the bedside system 110.

Workstation 116 includes a user interface 126 configured to receive user inputs to operate various components or systems of catheter procedure system 100. User interface 126 includes controls 118 that allow the user to control bedside system 110 to perform a catheter based medical procedure. For example, controls 118 may be configured to cause bedside system 110 to perform various tasks using the various percutaneous intervention devices with which bedside system 110 may be equipped (e.g., to advance, retract, or rotate a guidewire, advance, retract or rotate a working catheter, advance, retract or rotate a microcatheter, advance, retract, or rotate a guide catheter, inflate or deflate a balloon located on a catheter, position and/or deploy a stent, inject contrast media into a catheter, inject medicine into a catheter, or to perform any other function that may be performed as part of a catheter based medical procedure). Drive assembly 114 includes various drive mechanisms to cause movement (e.g., axial and rotational movement) of the components of the bedside system 110 including the percutaneous intervention devices. In an embodiment, the drive assembly 114, user interface 126 and/or controls 118 are used to manipulate a proximal end of the guidewire or catheter to direct a distal end of the device into the appropriate vessels toward a target location and avoid advancing into side branches.

In one embodiment, controls 118 include a touch screen 124, one or more joysticks 128 and buttons 130, 132. The joystick 128 may be configured to advance, retract, or rotate various components and percutaneous intervention devices such as, for example, a guidewire, a guide catheter, a microcatheter or a working catheter. Buttons 130, 132 may include, for example, an emergency stop button and a multiplier button. When an emergency stop button is pushed a relay is triggered to cut the power supply to bedside system 110. Multiplier button acts to increase or decrease the speed at which the associated component is moved in response to a manipulation of controls 118. In one embodiment, controls 118 may include one or more controls or icons (not shown) displayed on touch screen 124, that, when activated, causes operation of a component of the catheter procedure system 100. Controls 118 may also include a balloon or stent control that is configured to inflate or deflate a balloon and/or a stent. Each of the controls may include one or more buttons, joysticks, touch screen, etc. that may be desirable to control the particular component to which the control is dedicated. In addition, touch screen 124 may display one or more icons (not shown) related to various portions of controls 118 or to various components of catheter procedure system 100.

User interface 126 may include a first monitor or display 120 and a second monitor or display 122. First monitor 120 and second monitor 122 may be configured to display information or patient specific data to the user located at workstation 116. For example, first monitor 120 and second monitor 122 may be configured to display image data (e.g., x-ray images, MRI images, CT images, ultrasound images, etc.), hemodynamic data (e.g., blood pressure, heart rate, etc.), patient record information (e.g., medical history, age, weight, etc.). In addition, first monitor 120 and second monitor 122 may be configured to display procedure specific information (e.g., duration of procedure, catheter or guidewire position, volume of medicine or contrast agent delivered, etc.). Monitor 120 and monitor 122 may be configured to display information regarding the position the guide catheter. Further, monitor 120 and monitor 122 may be configured to display information to provide the functionalities associated with controller 134 (shown in FIG. 2). In another embodiment, user interface 126 includes a single screen of sufficient size to display one or more of the display components and/or touch screen components discussed herein.

Catheter procedure system 100 also includes an imaging system 104 located within lab unit 106. Imaging system 104 may be any medical imaging system that may be used in conjunction with a catheter based medical procedure (e.g., non-digital x-ray, digital x-ray, CT, Mill, ultrasound, etc.). In an exemplary embodiment, imaging system 104 is a digital x-ray imaging device that is in communication with workstation 116. In one embodiment, imaging system 104 may include a C-arm (not shown) that allows imaging system 104 to partially or completely rotate around patient 102 in order to obtain images at different angular positions relative to patient 102 (e.g., sagittal views, caudal views, anterior-posterior views, etc.).

Imaging system 104 may be configured to take x-ray images of the appropriate area of patient 102 during a particular procedure. For example, imaging system 104 may be configured to take one or more x-ray images of the heart to diagnose a heart condition. Imaging system 104 may also be configured to take one or more x-ray images (e.g., fluoroscopy) during a catheter based medical procedure (e.g., real time images) to assist the user of workstation 116 to properly position a guidewire, guide catheter, microcatheter, stent, etc. during the procedure. The image or images may be displayed on first monitor 120 and/or second monitor 122. In particular, images may be displayed on first monitor 120 and/or second monitor 122 to allow the user to, for example, accurately move a guide catheter into the proper position.

Figure 2:
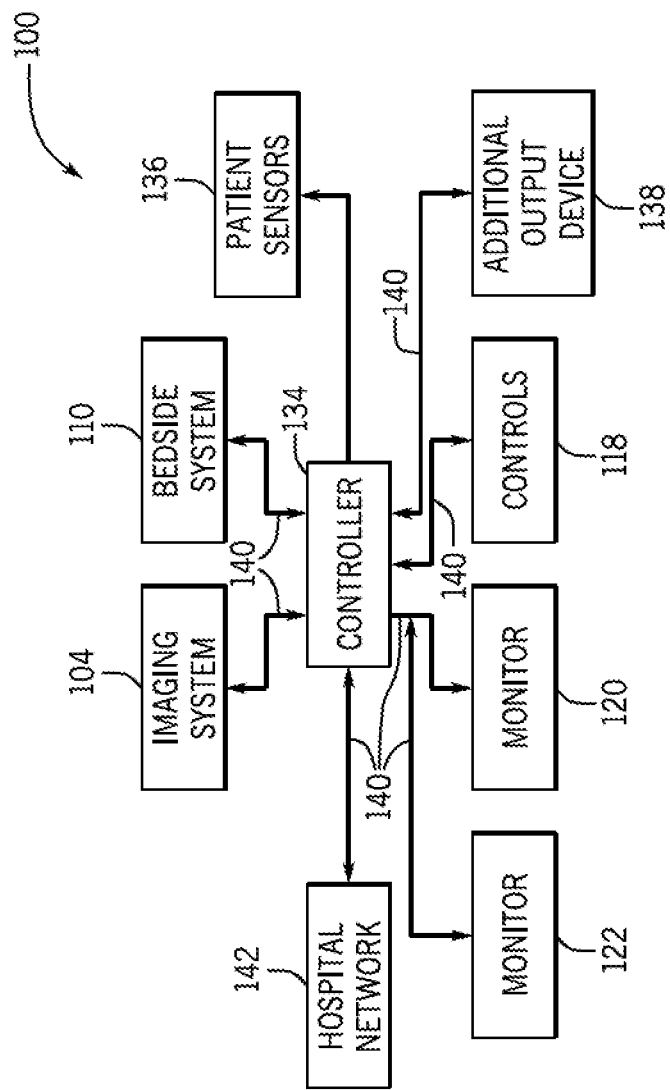
FIG. 2 is a schematic block diagram of an exemplary catheter procedure system in accordance with an embodiment.

Referring to FIG. 2, a block diagram of catheter procedure system 100 is shown according to an exemplary embodiment. Catheter procedure system 100 may include a control system, shown as controller 134. Controller 134 may be part of workstation 116. Controller 134 may generally be an electronic control unit suitable to provide catheter procedure system 100 with the various functionalities described herein. For example, controller 134 may be an embedded system, a dedicated circuit, a general-purpose system programmed with the functionality described herein, etc. Controller 134 is in communication with one or more bedside systems 110, controls 118, monitors 120 and 122, imaging system 104 and patient sensors 136 (e.g., electrocardiogram ("ECG") devices, electroencephalogram ("EEG") devices, blood pressure monitors, temperature monitors, heart rate monitors, respiratory monitors, etc.). In various embodiments, controller 134 is configured to generate control signals based on the user's interaction with controls 118 and/or based upon information accessible to controller 134 such that a medical procedure may be performed using catheter procedure system 100. In addition, controller 134 may be in communication with a hospital data management system or hospital network 142 and one or more additional output devices 138 (e.g., printer, disk drive, cd/dvd writer, etc.).

Communication between the various components of catheter procedure system 100 may be accomplished via communication links 140. Communication links 140 may be dedicated wires or wireless connections. Communication links 140 may also represent communication over a network. Catheter procedure system 100 may be connected or configured to include any other systems and/or devices not explicitly shown. For example, catheter procedure system 100 may include IVUS systems, image processing engines, data storage and archive systems, automatic balloon and/or stent inflation systems, medicine injection systems, medicine tracking and/or logging systems, user logs, encryption systems, systems to restrict access or use of catheter procedure system 100, etc.

As mentioned, controller 134 is in communication with bedside system 110 and may provide control signals to the bedside system 110 to control the operation of the motors and drive mechanisms used to drive the percutaneous intervention devices (e.g., guidewire, catheter, etc.). The bedside system 110 may include, for example, a guidewire axial drive mechanism that provides for advancement and/or retraction of a guidewire, a working catheter axial drive mechanism that provides for advancement and/or retraction of a working catheter and a guidewire rotational drive mechanism that is configured to cause a guidewire to rotate about its longitudinal axis. In one embodiment, the various drive mechanisms are housed in a drive assembly 114 (shown in FIG. 1).

Figure 3:
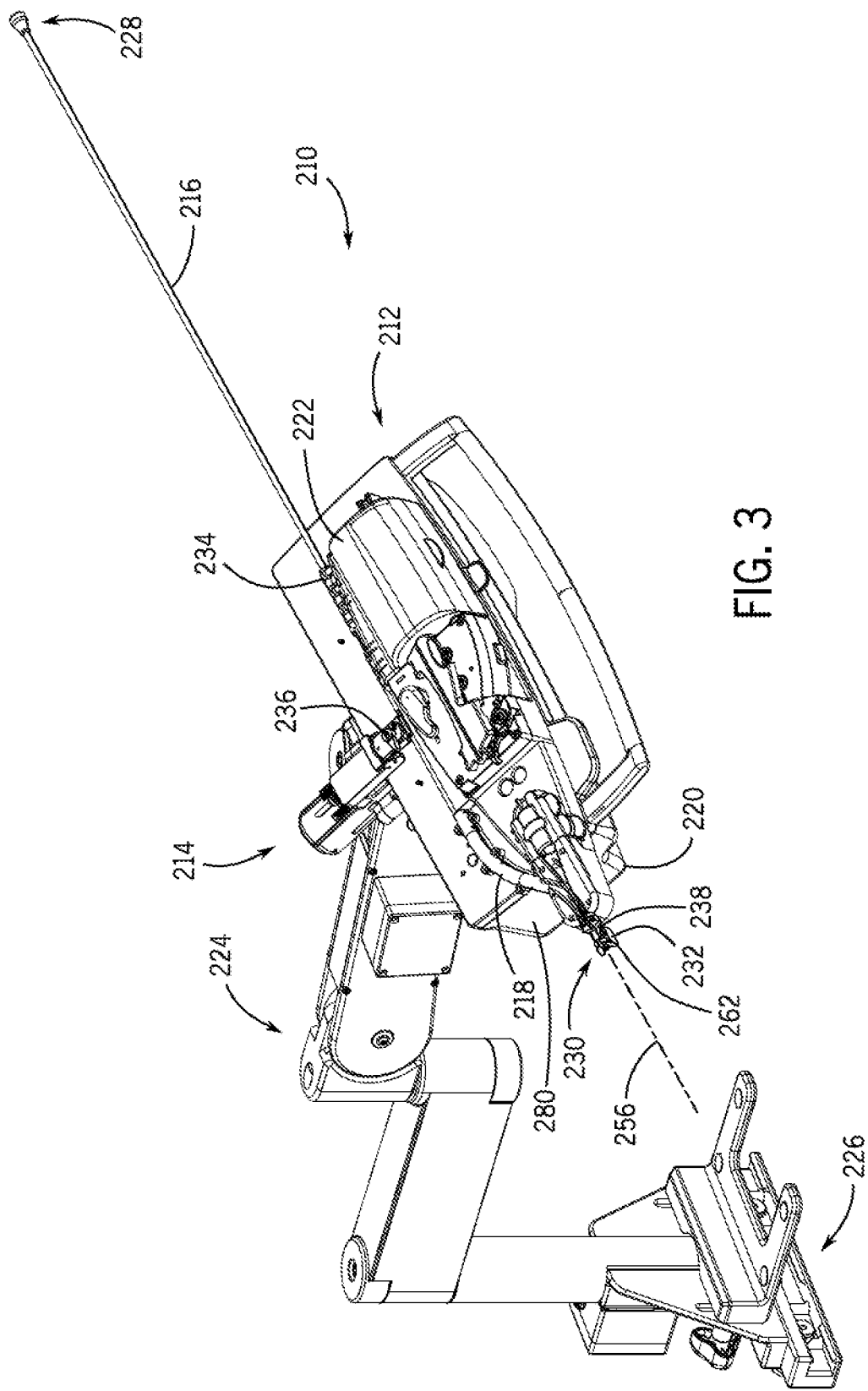
FIG. 3 is an isometric view of an exemplary bedside system of a catheter procedure system in accordance with an embodiment.

FIG. 3 is an isometric view of an exemplary bedside system of a catheter procedure system in accordance with an embodiment. In FIG. 3, a bedside system 210 includes a robotic mechanism 212 that may be used to robotically move an elongated medical device (e.g., percutaneous intervention devices or other components). The robotic mechanism 212 is moveable relative to a base 214. The robotic mechanism 212 includes a robotic drive base 220 movable relative to base 214 and a drive assembly 222 that is operatively secured to robotic drive base 220. In FIG. 3, the drive assembly 222 is shown as a cassette that houses the various drive mechanisms used to drive the percutaneous devices and that may be equipped with the percutaneous devices. In one embodiment, base 214 is secured to an articulating arm 224 that allows a user to position robotic mechanism 212 proximate a patient. In an embodiment, base 214 is the distal portion of the articulating arm 224. Articulating arm 224 is secured to a patient bed by a rail clamp or a bed clamp 226. By manipulation of articulated arm 224, the base 214 is placed in a fixed location relative to a patient that lies upon the patient bed. The joints of the articulated arm 224 can be locked once the desired location of the robotic mechanism 212 is set relative to the patient.

As used herein, the direction distal is the direction toward the patient and the direction proximal is the direction away from the patient. The term up and upper refers to the general direction away from the direction of gravity and the term bottom, lower and down refers to the general direction of gravity. The term front refers to the side of the robotic mechanism that faces a user and away from the articulating arm. The term rear refers to the side of the robotic mechanism that is closest to the articulating arm. The term inwardly refers to the inner portion of a feature. The term outwardly refers to the outward portion of a feature.

Bedside system 210 also includes a flexible track 216 that is movable along a rigid guide track 218 having a non-linear portion. The flexible track 216 includes a proximal end 228 and a distal end 230. The flexible track 216 supports an elongated medical device such as a guide catheter so that the guide catheter can be advanced into the patient without buckling. In one embodiment, drive assembly 222 includes structure that defines rigid guide 218. In another embodiment, base 214 alone or in combination with drive assembly 222 includes structure that defines rigid guide 218.

The flexible track 216 is initially positioned within the rigid guide 218 by feeding distal end 230 of flexible track 216 into a proximal opening 234 of rigid guide 218 until the distal end 230 of the flexible track 216 extends beyond a collar 258 of rigid guide 218. The collar 258 is formed at the distal end of rigid guide 218. The distal end 230 of flexible track 216 is operatively connected and secured to a sheath clip 232 which is releasably connected to drive assembly 222. The rigid guide 218 includes a linear portion beginning at proximal opening 234 and a non-linear portion. In one embodiment, the non-linear portion is an arcuate portion having at least one point of inflection.

To perform a procedure, the sheath clip 232 is pulled by a user away from drive assembly 222 in a direction along longitudinal axis 256 until the distal end 262 of sheath clip 232 is proximate the patient. In one embodiment, an introducer (not shown) is secured to the distal end 262 of the sheath clip 232. The introducer is a device that is secured to a patient to positively position the introducer to the patient to allow insertion or removal of elongated medical devices such as a guide catheter, guidewire and/or working catheter into the patient with minimal tissue damage to the patient. Once the operator has pulled the sheath clip 232 and accompanying flexible track 216 toward the patient such that the introducer is proximate the patient, the flexible track 216 is locked in position by a locking clamp 236. The locking clamp 236 secures the flexible track 216 to base 214 such that a portion of flexible track 216 is in a fixed position relative to the patient bed and the patient to the extent the patient lies on the patient bed.

During one type of intervention procedure, a guide catheter (not shown) is inserted into a patient's femoral artery through an introducer and positioned proximate a coronary ostium of a patient's heart. The guide catheter maintains a linear position along its longitudinal axis 256 within drive assembly 222 and for a certain distance distal drive assembly 222. In one embodiment, longitudinal axis 256 corresponds to the longitudinal axis of drive assembly 222. During a medical procedure such as percutaneous coronary intervention (PCI), a guide catheter (not shown) is used to guide elongated medical devices such as a guidewire and balloon stent catheter into a patient to conduct, for example, an exploratory diagnosis or to treat a stenosis within a patient's vascular system. As mentioned, the distal end of the guide catheter may be seated within the a coronary ostium of the patient's heart. Robotic mechanism 212 drives a guidewire and/or a working catheter such as a balloon stent catheter in and out of a patient. The guidewire and working catheter are driven within the guide catheter between the distal end of the robotic mechanism 212 and the patient. In one embodiment, longitudinal axis 256 is the axis about which the drive assembly 222 causes rotation of a guidewire and the axis along which the drive assembly 222 drives the guidewire along its longitudinal axis and drives a working catheter such as a balloon stent catheter along its longitudinal axis.

Figure 4:
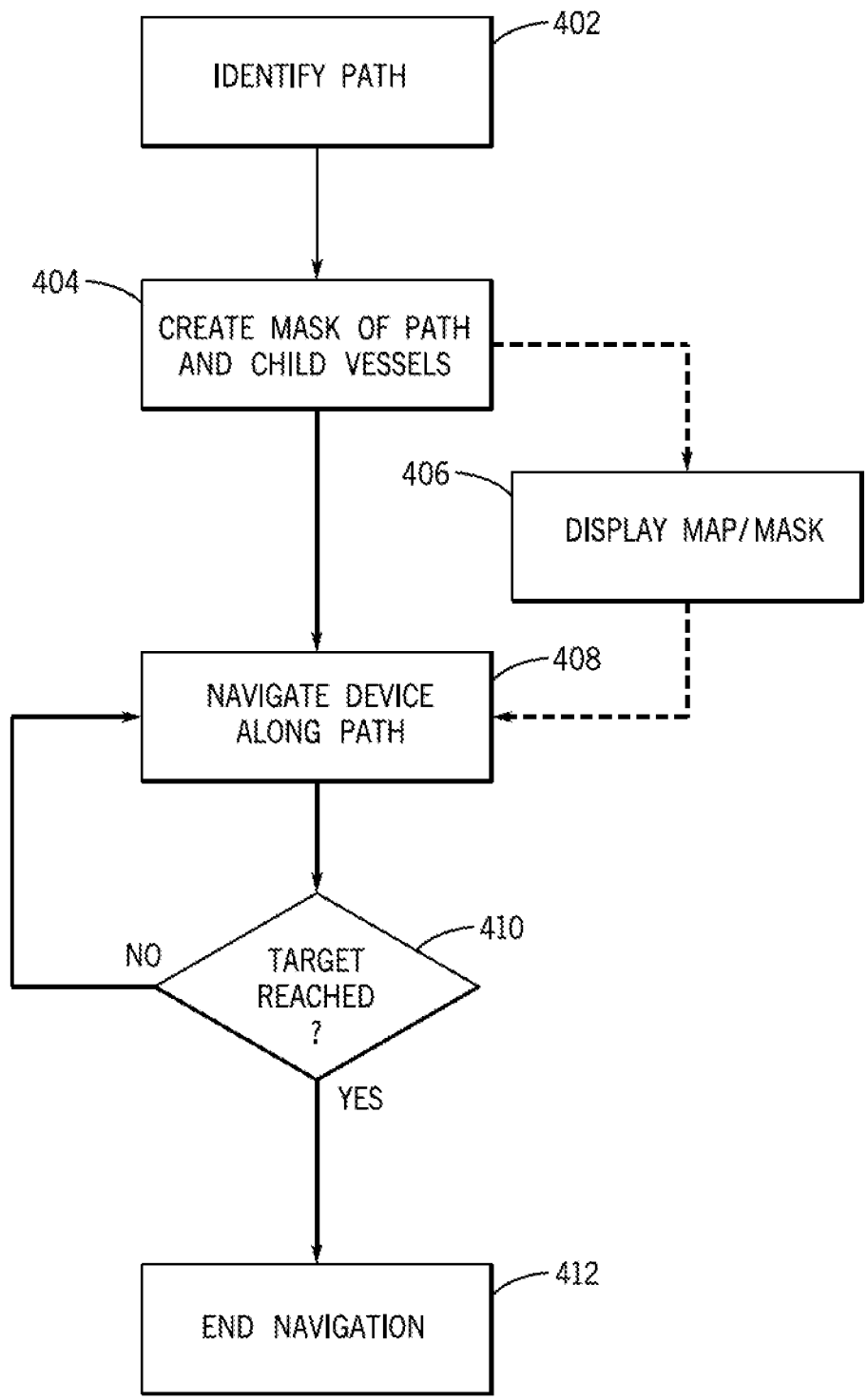
FIG. 4 illustrates a method for visualization of a path and navigation of an elongated medical device in accordance with an embodiment.
Figure 5:
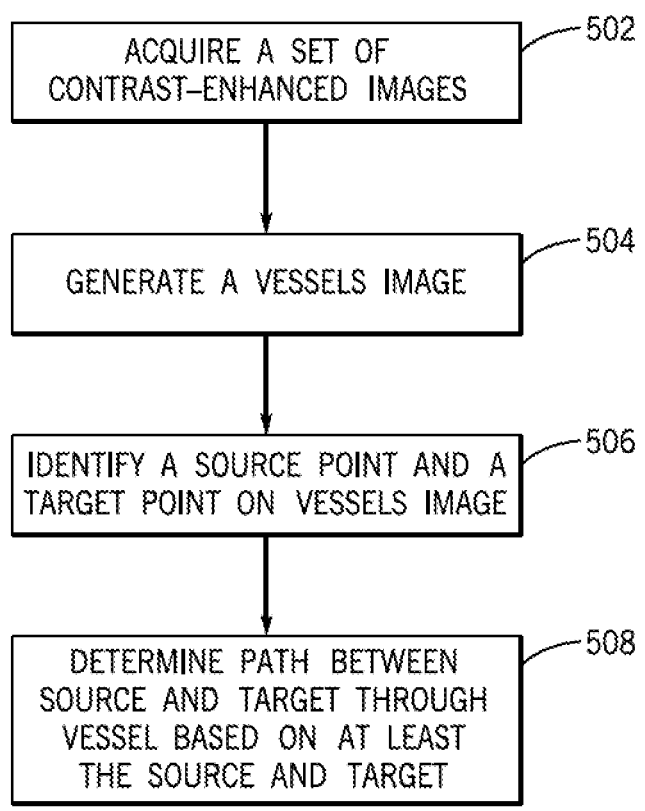
FIG. 5 illustrates a method for identifying a path through a vessel in accordance with an embodiment.

FIG. 4 illustrates a method for visualization of a path and navigation of an elongated medical device in accordance with an embodiment. At block 402, a path through the vasculature is identified or detected. In one embodiment, the path is a path through a vessel or vessel(s) to reach a target location, for example, a lesion. FIG. 5 illustrates a method for identifying a path through a vessel in accordance with an embodiment. At block 502, a set of images or image data of a region of interest is acquired using an imaging system (e.g., imaging system 104 shown in FIG. 1). In an embodiment, the images are contrast-enhanced images that are obtained by injecting a contrast agent or media into the patient before and/or during the image acquisition. In an embodiment, the set of images may include images acquired at one or more views of the region of interest (e.g., sagittal views, caudal views, anterior-posterior views, etc.). In various embodiments, the set of images may be acquired during at least one phase of a physiological cycle such as a heart cycle or a respiratory cycle. The following description herein will refer to an exemplary heart cycle. For example, image data for the set of images may be acquired during a single phase of the heart cycle, during a plurality of phases of the heart cycle or during all of the phases of the heart cycle. Information regarding the state of the physiological cycle may be provided by a patient sensor (e.g., patient sensors 136 shown in FIG. 2) such as, for example, an ECG or EEG for the heart cycle. At block 504, a vessels-image is generated based on at least the set of acquired contrast-enhanced images. In one embodiment, the vessels-image is a two-dimensional image. A two-dimensional vessels-image may be generated, for example, by performing a vessel extraction from at least one image from the set of images. In an embodiment, an optimal view may be selected from the set of images if the set of images includes more than one view. In one embodiment, the eigenvalues of the image Hessian may be used as a "vesselness" measure, for example, a Frangi filter. Additional filtering may be performed based on object area (e.g., filter out objects with small shapes) and non-linear objects (e.g., filter out objects that are not similar to a line shape). A control system or controller of the catheter procedure system (e.g., controller 134 shown in FIG. 2) may be configured to generate the two-dimensional vessels-image as described above.

Figure 6:
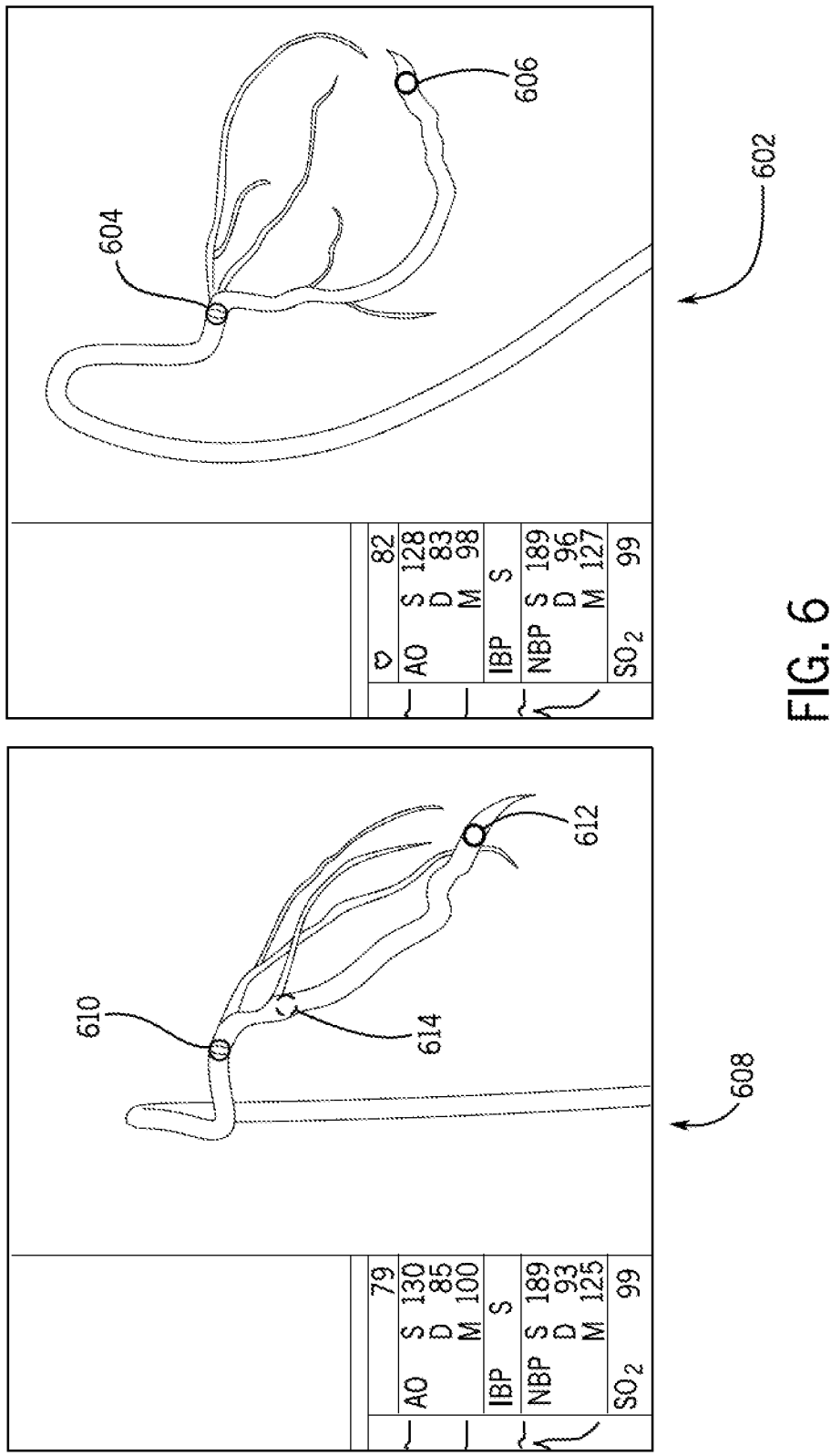
FIG. 6 illustrates the identification of exemplary source and target points on a vessels-image in accordance with an embodiment.

At block 506, a source point or location and a target point or location are identified on the vessels-image. FIG. 6 illustrates the identification of exemplary source and target points on a vessels-image in accordance with an embodiment. In FIG. 6, a source point or location 604 and a target point or location 606 are identified on a vessels-image 602. In one embodiment, the source point or location is a starting point for the path such as a coronary ostium or a distal end of a guide catheter. The target point or location may be, for example, a lesion in a vessel or a point just before or past the lesion in a vessel. The source point 604 and the target point 606 may be identified using, for example, an input or controls of a user interface of the catheter procedure system (e.g., user interface 126 shown in FIG. 1). In another embodiment, one or more additional constraint points along the path may also be identified. In FIG. 6, a source point 610 a target point 612 and a constraint point 614 are identified on a vessel-image 608. The additional constraint points may be identified using, for example, an input or controls of a user interface of the catheter procedure system (e.g., user interface 126 shown in FIG. 1).

Returning to FIG. 5, at block 508 a path between the source point and the target point through the vessel is determined. In an embodiment, the path is determined by calculating a shortest path between the source point and the target point through the vessel(s). For example, a directed, weighted graph may be generated from a skeleton of the vessels-image. The shortest path on the directed graph (e.g., based on weights and/or a cost function) may then be calculated from the source point to the target point. In addition, the length (or distance) of the identified path through the vessel(s) from the source point to the target point may be determined. If additional constraint points have been provided, the shortest path may be calculated between each pair of consecutive points. All calculated paths may then be accumulated to a single path from the source point to the target point on the directed graph that goes through all of the constraint points. Constraint points may be identified by an operator with the source point and the target point at block 506 or the user or operator may provide constraint points if the path is not identified correctly. For example, the identified path may be displayed (e.g., in a 2D or 3D image) to a user using a display (e.g., display 120, 122 shown in FIG. 1) and the user may either approve the path using an input of a user interface or may provide one or more additional constraint points using the user interface. The process at block 508 is then repeated with the additional constraint points. In another embodiment, the path may be smoothed or corrected based on the bending energy of the guidewire or other elongated medical device. For example, a directed graph may be generated that connected a set of sampled points along the vessel traversed by the path. The graph weights may be set to the estimated local bending energy of the guidewire or other elongated medical device, which is related to the local bending angle between each two vectors. The path may then be calculated by determining the shortest path which minimizes the local bending energy from the source point to the target point. An example of a method to smooth a path based on bending energy is described in S. Schafer, V. Singh, P. B. Noel, A. M. Walczak, J. Xu and K. R. Hoffmann, "Real-time endovascular guidewire position simulation using shortest path algorithms", Int J. CARS 4, pp. 597-608 (2009), herein incorporated by reference in its entirety.

Figure 11:
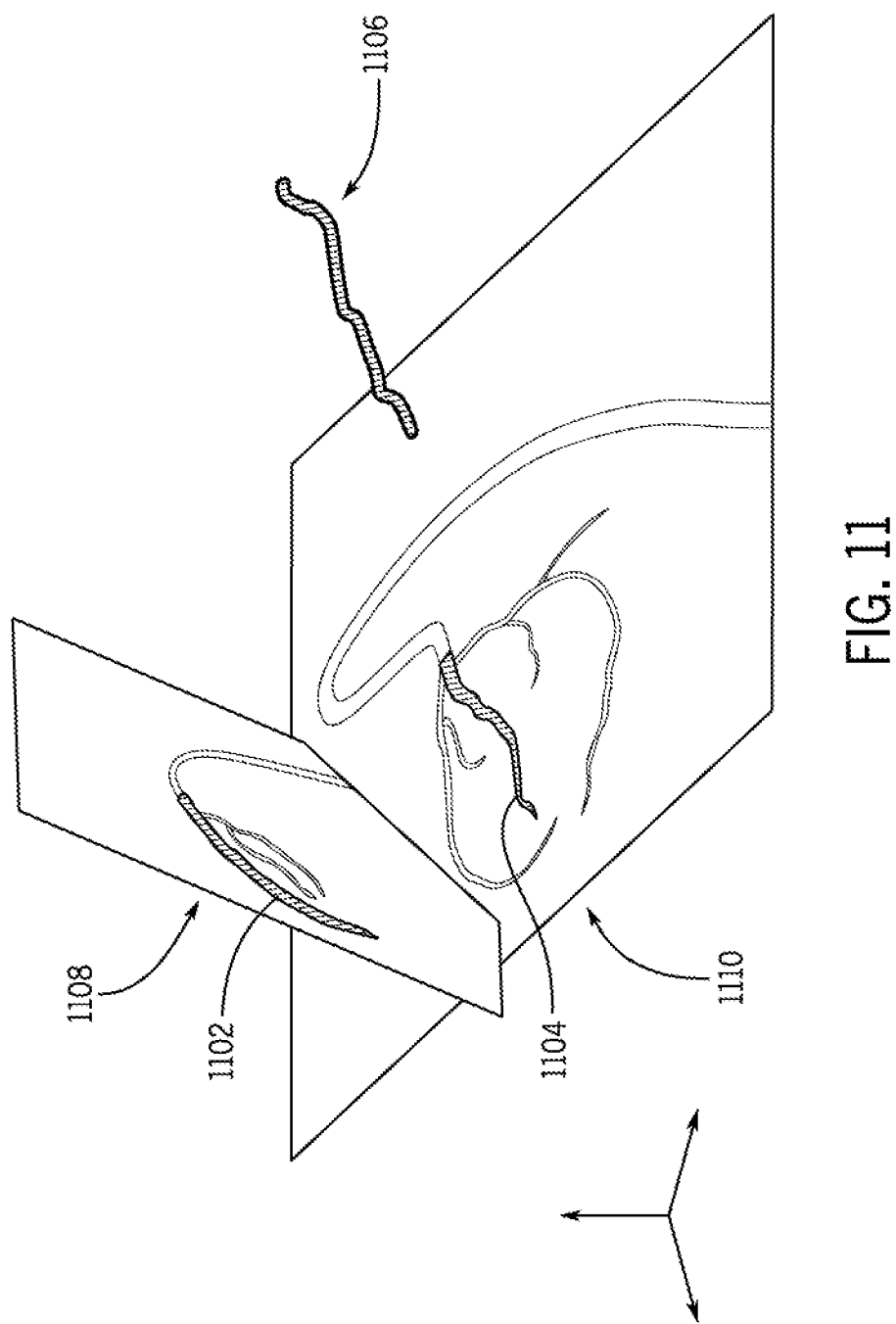
FIG. 11 illustrates first and second two dimensional views of a path and a generated three dimensional path in accordance with an embodiment.

In another embodiment, a three-dimensional path may be generated. The three-dimensional path may be generated using two different views from the set of images, for example, a first image at a first view and a second image at a second view. A first two-dimensional vessels-image may be created using the first image at the first view and a second two-dimensional vessels-image may be created using the second image at the second view. In an embodiment, the first two-dimensional vessels-image and the second two-dimensional vessels-image may be generated as described above with respect to step 504. The path through the vessel of interest between a source point and a target point is determined for the first vessels-image and the path is determined for the second vessels-image as described above with respect to steps 506 and 508. FIG. 11 illustrates first and second two dimensional views of a path and a generated three dimensional path in accordance with an embodiment. A three-dimensional path 1106 may then be generated using the path 1102 for the first two-dimensional vessels-image at the first view and the path 1104 for the second two-dimensional vessels-image at the second view. In one embodiment. the three dimensional path is generated by first projecting the first 2D vessels-image 1108 onto the 3D space and projecting the second vessel image 1110 onto the 3D space based on a set of parameters of the imaging system (e.g., parameter of a C-arm). Next, for each point in a set of points on the path in the first vessels-image, a set of epipolar lines are calculated on the second vessels-image, and the most probable matching points on the other path are determined using, for example, the Viterbi algorithm. For each two matching points in the two views, a common point is found in 3D space thereby reconstructing a three-dimensional path.

If the vessel through which the path passes is in an area of the vasculature that is not impacted by movement caused by a physiological cycle, then the path is not dependent on phases of a physiological cycle. In another embodiment, the path is determined for a single phase of a heart cycle or other physiological cycle. In another embodiment, the path is determined for all phases of the heart cycle or other physiological cycle. In an embodiment where the vessel is impacted by the heart cycle, the starting point of the heart cycle may be selected, for example, using R-phase gating and the acquired images synchronized to an R-wave peak. If image data is acquired for less than all phases of the heart at block 502, data may be interpolated from the acquired image data and used to identify the path for all phases of the heart cycle. In an embodiment, to determine the path for all phases of the heart, the path may be tracked between adjacent frames utilizing, for example, matching points or Viterbi algorithm. A control system or controller of the catheter procedure system (e.g., controller 134 shown in FIG. 2) may be configured to determine a path from the source point to the target point as described above.

Figure 12B:
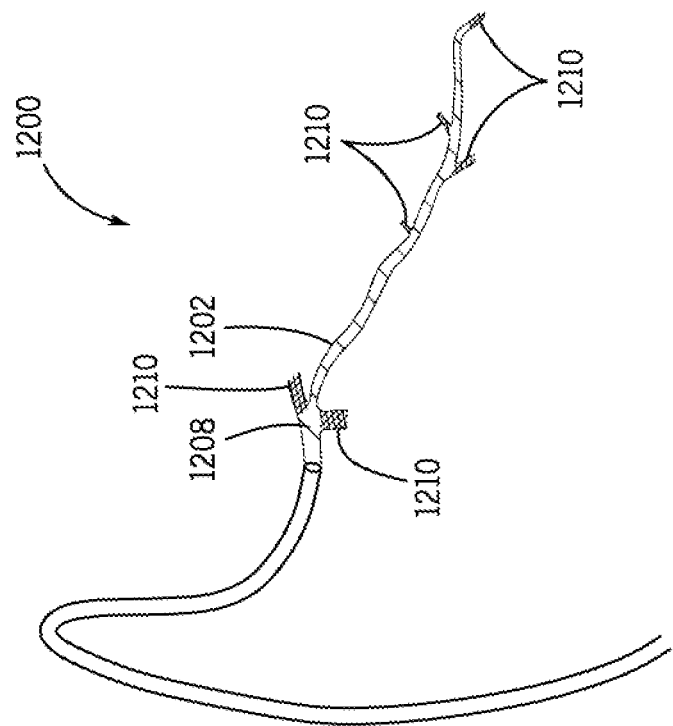
FIG. 12B illustrates the vasculature of FIG. 12A after a vessel mask and child vessel mask have been applied and displayed.
Figure 12A:
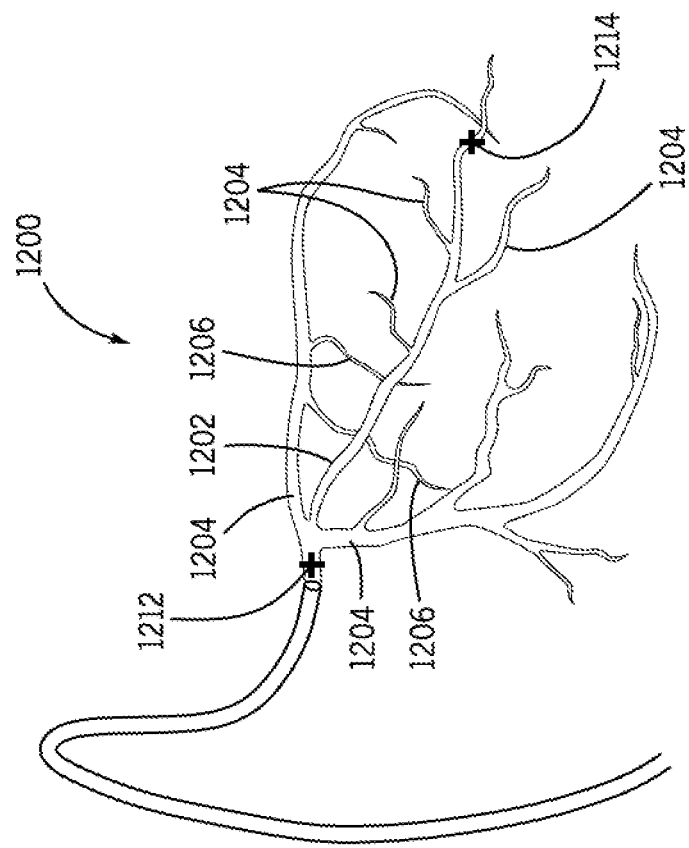
FIG. 12A illustrates a vasculature having child vessels and branches that cross or are connected via a bifurcation to a vessel in an identified.

In an embodiment, determining the path from the source point to the target point through a vessel at block 508 also includes identifying child vessels or branches of the path vessel(s) where the child vessels or branches are not part of the identified path between the source point and the target point but are connected via a bifurcation to a vessel in the identified path. Accordingly, the child vessels or branches represent an incorrect or wrong path. The child vessels or branches may be identified or detected based on contrast enhanced image data acquired at step 502. In addition, the child vessels or branches may be distinguished from crossover vessels which appear to overlap the path vessel(s) or are appearing to be overlapped by the path vessels but are not directly connected to the path vessel. In one embodiment, the child vessels or branches may be identified based on appearance of the contrast agent in the acquired images. For example, a child vessel or branch fills with contrast after the main path vessel and a crossover vessel fills with contrast before the main path vessel. If the branch is a child vessel in direct fluid communication with the vessel then the contrast in the child vessel will be viewed as occurring immediately after the contrast is viewed in the portion of the vessel to which it is in fluid communication. In one embodiment contrast that appears in the branch either earlier or a predetermined time later will be identified as a non-connecting crossover branch. An image or images(s) including the identified path from the source point to the target point and any identified child vessels may be reconstructed using either two-dimensional reconstruction or three-dimensional reconstruction. Referring to FIG. 12A an image of a vasculature 1200 includes vessels extending from a source 1212 to a target 1214. In one embodiment vessel 1202 is in the path that extends from source 1212 to target 1214. Though it is possible that a number of vessels are included in the path that extends from source 1212 to target 1214. Child vessels 1204 are in direct fluid communication to the vessel(s) identified in the path between the source and target. Branches 1206 that appear in a 2D image to cross over or under the path vessels but are not in direct fluid communication are referred to as non-connecting branches. As discussed above the child vessels 1204 and non-connecting branches 1206 are identified using the process outlined or other methods known in the art. Referring to FIG. 12B once child vessels 1204 and branches 1206 are identified a vessel mask 1208 is applied and displayed on an image associated with the path mask. Child vessel mask 1210 is applied and displayed on the image associated with the path mask. In one embodiment child vessel mask covers only the portion of child vessels 1204 closely adjacent vessel 1202. Vessel mask 1208 is applied and displayed from a source point 1212 to a target point 1214 as illustrated in FIG. 12A. The image or image(s) may be used as a reference image and displayed to the user of the catheter procedure system on a display (e.g., display 120,122 shown in FIG. 1). A control system or controller of the catheter procedure system (e.g., controller 134 shown in FIG. 2) may be configured to identify child vessels or non-connecting branches and generate an image with the identified path and child vessels as described above.

Figure 7:
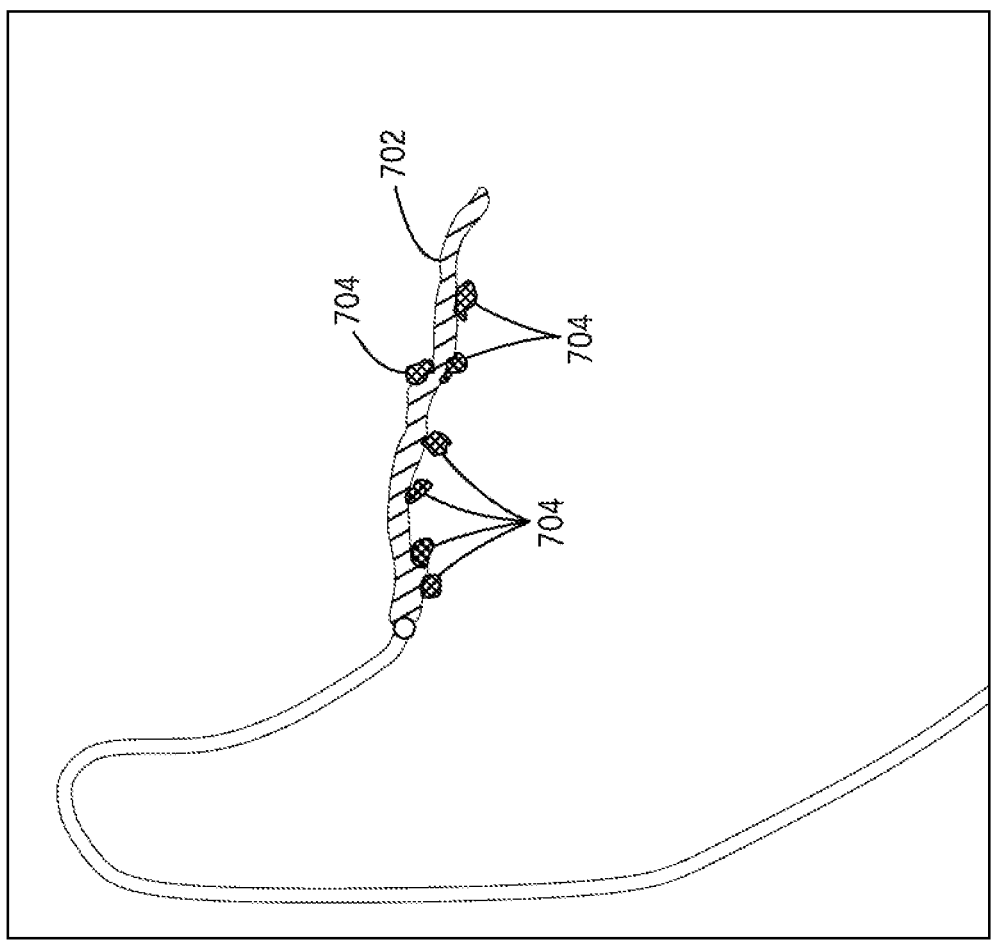
FIG. 7 illustrates an exemplary path mask and child vessel mask in accordance with an embodiment.

Returning to FIG. 4, once the path through the vessel(s) from the source point to the target point is identified, a map or mask of the identified path is created at block 404. In an embodiment, the mask is applied as a translucent overlay that allows a user or operator to visualize or allows the system to track the device being navigated in the vessel along the path or off path. Applying the mask to the image obviates the need for contrast, as the path can be visualized. In one embodiment, the mask is displayed by highlighting the path. In this manner, the path is displayed in a way that stands out on a display. In addition, a mask of the identified child vessels or branches may also be created, referred to herein as child-vessel mask. If the vessel is impacted by a physiological cycle such as the heart cycle, in one embodiment, the mask may be created for a single phase of the heart cycle or other physiological cycle. In another embodiment, a mask may be created for each of the phases of the heart cycle or other physiological cycle. In one embodiment, the masks of the path and the child vessels may be two-dimensional. In one embodiment, a vessel mask for the path (and/or child vessels) may be created around the identified path using, for example, a minimum cost contour detection algorithm (MCA) to locate the edges of the vessel and smooth the edges of the vessel. Vessel curvature may be determined by mapping pixels to a "vertical" image that is based on local path curvature properties. After the edges are found and smoothed, a path center-line may be corrected to be the center of mass of each pair of edge points. Other mask boundaries may be estimated by connecting the edges of the mask in the direction perpendicular to the vessel direction. The area inside these lines may then be painted and a morphological opening identified. FIG. 7 illustrates an exemplary path mask and child vessel mask in accordance with an embodiment. In FIG. 7, a path mask 702 is shown with a first cross-hatching overlaid on the identified path in an image (e.g., a reference image or a real-time image). The reference image or real-time image may be two-dimensional or three-dimensional. A plurality of child vessel masks 704 are shown with a second cross-hatching overlaid on a plurality of identified child vessels or branches in the image. In one embodiment, the path mask 702 and the child vessel mask 704 may be indicated on the image using different colors. In an embodiment vessel mask 704 covers only the portion of the child vessel closely adjacent the path 702. In one embodiment vessel mask 704 covers a substantial portion of the child vessel. As mentioned above, as mask may be created for the path and the child vessels for each phase of the heart cycle so that the mask for the path and child vessels may appropriately change with time, e.g., through the heart cycle. Accordingly, an appropriate mask may be displayed (e.g., overlay the mask on a reference image or real time image) during all phases of the heart cycle. A control system or controller of the catheter procedure system (e.g., controller 134 shown in FIG. 2) may be configured to create masks of the identified path and child vessels as described above.

At block 406, the path mask and child vessels mask may be displayed (e.g., on a display 120, 122 shown in FIG. 1) to an operator of the catheter procedure system. For example, the path mask and child vessels mask may be used to assist an operator with manual navigation of an elongated medical device, to assist with navigation of the elongated medical device by an operator using the catheter procedure system or to allow an operator to monitor navigation if the navigation is fully automated using the catheter procedure system. If the navigation is fully automated the path mask and child vessel mask are not required to be displayed to the operator at block 406 or during navigation as described below. As mentioned above, the mask of the path and the mask of the child vessels or branches may be overlaid on a reference image where the mask corresponds to the phase of the reference image or the path mask and the child vessels mask may be overlaid on a real-time image with no contrast where the masks correspond to the phase of the heart for the particular real time image. Accordingly, the path mask and child vessels mask may change appropriately with any change in the identified path and child vessels during the phases of the heart cycle.

Figure 8:
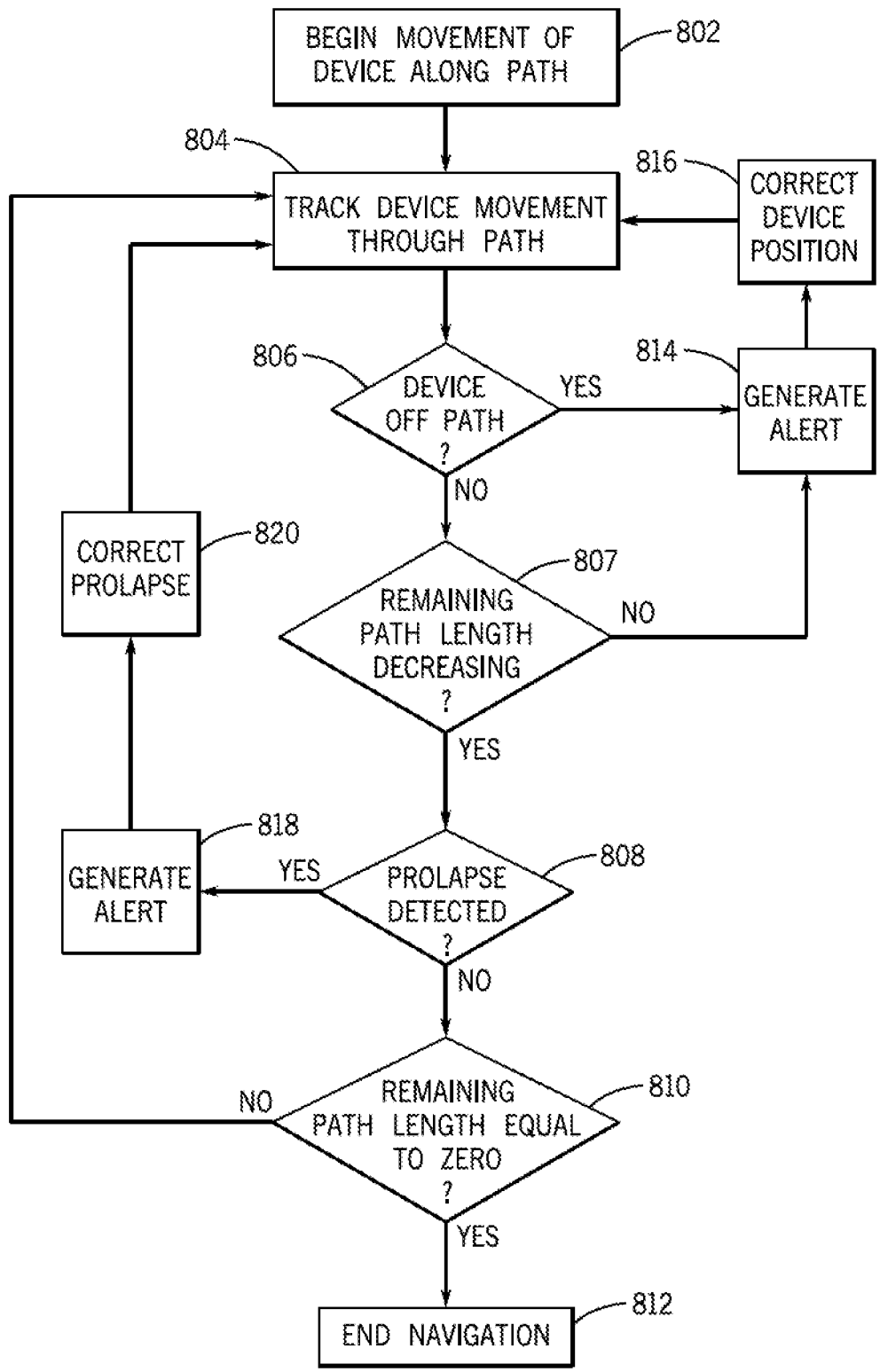
FIG. 8 illustrates a method for delivering an elongated medical device to a target location in accordance with an embodiment.

At block 408, the elongated medical device is navigated along the identified path using the catheter procedure system. In one embodiment, the elongated medical device is navigated in a fully automated manner using the catheter procedure system. In another embodiment, the operator may view the mask of the identified path and child vessels and device tracking information described further below to assist the operator in the navigation and delivery of the elongated medical device along the path to a target location using the catheter procedure system. FIG. 8 illustrates a method for delivering an elongated medical device to a target location in accordance with an embodiment. At block 802, movement of the device is begun, for example, an operator may provide an input via a user interface to start a fully automated process or an operator may utilize the user interface to control movement of the device. The description below will refer navigation of an exemplary guidewire, however, it should be understood that the techniques described herein may also be used for navigation of other elongated medical devices such as, for example, a working catheter (e.g., a balloon catheter or stent delivery system), a microcatheter or lesion treatment device. A control system or controller of the catheter procedure system (e.g., controller 134 shown in FIG. 2) may be configured to perform some or all of the portions of the method of delivering an elongated medical device to a target location as described below. While the guidewire is moving, the position of the guidewire is tracked at block 804. In one embodiment, an imaging system may be used to track a distal portion of the guidewire. In one embodiment, the distal portion of the guidewire includes a tip of the guidewire. The distal portion of the guidewire may be radiopaque and the position of the distal portion of the guidewire may be tracked using images acquired during navigation using the imaging system (e.g., imaging system 104 shown in FIG. 1). In one embodiment, the image are fluoroscopic images taken without contrast.

Figure 9:
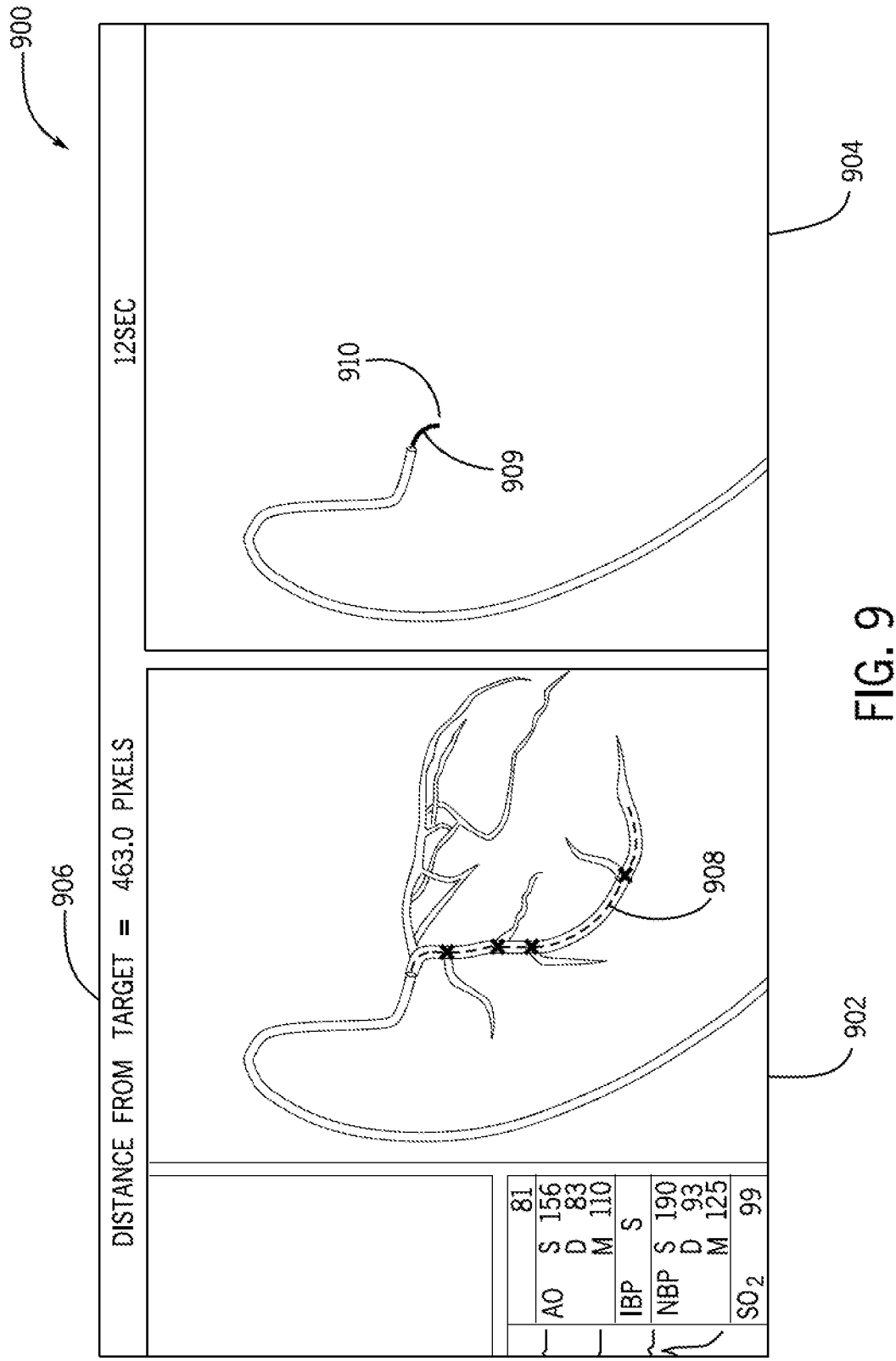
FIG. 9 shows an exemplary display illustrating a path and tracking a guidewire through the path in accordance with an embodiment.

As the guidewire moves through the path vessel(s) and the distal portion of the guidewire is tracked, a remaining path length is determined and updated based on the position of the distal portion of the guidewire. As used herein, the remaining path length is the distance between the distal portion of the guidewire (or other elongated medical device) and the target point or location through the identified path when the distal portion is on the identified path. As the distal portion of the guidewire advances towards the target point from the source point through the identified path, the remaining path length decreases. In an embodiment, the procedure may require use of a microcatheter in addition to the guidewire. In such an embodiment, the guidewire and the microcatheter may be advanced through the path in an alternating step wise fashion from the source point to the target point. The location of the distal portion of the guidewire may be projected or displayed on an image including the path and child vessels mask. FIG. 9 shows an exemplary display illustrating a path and tracking a guidewire through the path in accordance with an embodiment. In FIG. 9, a display includes a first view 902 and a second view 904. The display may be displayed to an operator on a display of the catheter procedure system (e.g., display 120, 122 shown in FIG. 1). The first view 902 shows a reference image and a mask 908 of a path shown as a dashed line, with potential branches along the path shown with an "X". The second view 904 shows a real-time image showing the movement and position of a distal portion 910 of the guidewire as it moves through the path. In an alternative embodiment, a display may include one view that shows a real-time image with both the masks (path and child vessels) and the guidewire tracking. While not shown in FIG. 9, a child vessels mask may also be shown in the display. Display 900 also shows a remaining path length 906. The remaining path length is calculated in pixels although other measures may be used in other embodiments. As the guidewire moves along the path towards the target point, the remaining path length 906 will be shown as decreasing towards zero. Finally, a portion 909 of the guidewire can be indicated by showing its progress along mask 908 of a path.

At block 806, it is determined whether the distal portion of the guidewire is off path based at least on the remaining path length. If the remaining path length is decreasing and is greater than but not equal to zero, the guidewire continues to advance. In an embodiment, the velocity of the guidewire as it moves is determined using a control law based on the remaining path length. The control law may be a negative feedback control law and may be chosen so that the resulting system is stable (e.g., Lyapunov stable). The relationship between the command velocity and the negative of the remaining path length is a passive relationship. Therefore, an appropriate feedback control law based on the negative of the remaining path length is also passive (for the linear time invariant case it is also positive real). A passive control law is one that satisfies that the integral of the product of the input and the output is positive. Accordingly, for a control law based on the negative remaining path length the input is the negative remaining path length and the output is the negative velocity. In one example control law, the velocity may be proportional to the remaining path length, namely, as the remaining path length decreases, the velocity of the device decreases. In other examples, the velocity may be proportional to the remaining path length with saturation limits (e.g., limits based on the maximum allowable velocity for the guidewire or other device), the velocity may be scaled by a continuously smooth function such as a hyperbolic tangent function, the velocity may be scaled by cubic mappings, or the velocity may be scaled by cubic mappings with saturation limits. Examples of methods to control positive real (or passive) systems are described in Kottenstette, Nicholas, et al. "On relationships among passivity, positive realness, and dissipativity in linear systems." Automatica 50.4 (2014): 1003-1016, herein incorporated by reference in its entirety. In another embodiment, the velocity of the guidewire may also be adjusted based on local properties of the path such as tortuosity or narrowing.

At block 806, various parameters may be used to determine if the guidewire is off path. In one embodiment, if the remaining path length is less than zero (a negative number), the device is off path. For example, a device may be off path if it is moving down a child vessel or branch that is not part of the identified path to the target point or if it has gone past the target point. If the guidewire goes off the identified path, the remaining path length transitions from a positive number to a negative number that increases in a negative direction to indicate the distance the distal portion of the guidewire has traveled down the branch vessel which is not on the path. If the guidewire goes past the target point, the remaining path length will transition from a positive number to a negative number and the remaining path length will increase in the negative direction to indicate the distance the distal portion of the guidewire has moved past the target point. The change of the remaining path length from a positive number to a negative number may be displayed to the operator, for example, in FIG. 9, the display 900 may show the remaining path length 906 as a negative number.

At block 807, if the remaining path length is not decreasing, it may indicate that the distal portion of the guidewire has stopped moving and corrective action is required. For example, if the proximal end of the guidewire is being fed into the patient by the catheter procedure system but there is no movement of the distal portion of the guidewire corrective action may be required to change the position of the distal portion of the guidewire. If guidewire is off path at block 806 or if the remaining path length is not decreasing at block 807, the catheter procedure system generates an alert at block 814. The alert may be displayed to the operator of the catheter procedure system on a display (e.g., display 120, 122 shown in FIG. 1) and/or the alert may be audible. In another embodiment, the procedure may be stopped and an alert displayed to the operator so the operator may take corrective action. In another embodiment, the catheter procedure system may automatically take corrective action.

The position of the guidewire or distal portion of the guidewire is corrected at block 816. In one embodiment, when the remaining path length transitions to a negative number, the velocity of the guidewire becomes a negative number proportional to the remaining path length so the distal portion of the guidewire may be retracted. For example, the guidewire may be retracted until the distal position of the guidewire is positioned back on the path at the junction before the branch or retracted to back up to the target point. In another example, the guidewire may be rotated and retracted until the distal portion of the guidewire is positioned back on the path at the junction before the branch or retracted to the target point. Another example of a corrective action is to adjust the position of the distal end of the guide catheter to redirect the guidewire down the correct path. The distal portion of the guidewire may also be "wiggled" to get past upcoming branches that are off path. In one embodiment, the catheter procedure system automatically executes the corrective action to reposition the distal portion of the guidewire. In another embodiment, an operator controls the guidewire to adjust the position of the distal portion of the guidewire by providing input commands using the user interface of the catheter procedure system. In one embodiment, corrective action may be repeatedly taken by the operator or automatically by the catheter procedure system until the position of the guidewire is corrected. For example, if a first retraction of the guidewire does not place the distal portion of the guidewire on path, the guidewire may be retracted again. In an embodiment, different types of corrective action may be taken in succession until the position of the distal portion of the guidewire is on path. For example, the guidewire may first be retracted and then may be rotated and retracted. Once the position of the distal portion of the guidewire is corrected at block 816, advancement of the guidewire along the path resumes and the process continues at blocks 804 to track the movement of the device through the path.

Figure 10:
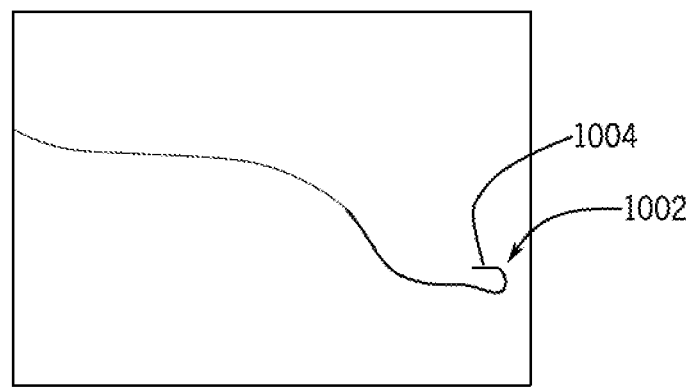
FIG. 10 illustrates exemplary types of wire prolapse in accordance with an embodiment.
Figure 10:
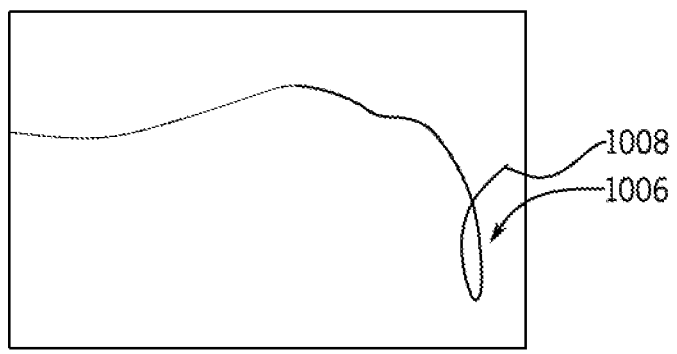

Returning to block 806, if the guidewire is on path, the movement of the guidewire along the path continues. At block 807, if the remaining path length is decreasing, the movement of the guidewire along the path continues. A guidewire or other elongated medical device may experience a prolapse while being advanced through the vasculature. At block 808, if there is a prolapse of the distal portion of the guidewire detected, an alert is generated at block 818. The alert may be displayed to the operator of the catheter procedure system on a display (e.g., display 120, 122 shown in FIG. 1) and/or the alert may be audible. In an embodiment, a prolapse may be detected by examining the distal portion of the guidewire using the imaging system. FIG. 10 illustrates exemplary types of wire prolapse in accordance with an embodiment. In FIG. 10, an open prolapse 1002 and a closed, full loop prolapse 1006 are shown. An open prolapse 1002 is a condition where the distal portion 1004 of the guidewire is bent but there is not a full loop. In one embodiment, an open prolapse 1002 may be detected by checking the curvature of the distal portion 1004 of the guidewire. A closed prolapse 1006 is a condition where there is a full loop of the distal portion 1008 of the guidewire. In an embodiment, a closed loop prolapse 1006 is detected using morphological filling. An image of the distal portion 1006 is subtracted from a "filled" image to check for a loop hole. In another embodiment, a prolapse may be detected using information from a previous image, for example, to detect if the distal portion of the guidewire is transitioning to a prolapse. A detected prolapse may be corrected at block 820. The catheter procedure system may be configured to provide the operator with suggested techniques for how to proceed to correct the prolapse at block 820. For example, various navigation techniques may be used to correct a prolapse such as a "knuckling" technique, halt and back up the device, halt and rotate the device, or rotate and retract the device. In one embodiment, the catheter procedure system automatically executes the corrective action to correct a prolapse of a distal portion of the guidewire. In another embodiment, an operator controls the guidewire by providing input commands using the user interface of the catheter procedure system. In one embodiment, corrective action may be repeatedly taken by the operator or automatically by the catheter procedure system until the prolapse is corrected. For example, if a first retraction of the guidewire does not correct the prolapse, the guidewire may be retracted again. In an embodiment, different types of corrective action may be taken in succession until the prolapse is corrected. For example, the guidewire may first be halted and backed up and then a knuckling technique may be used. Once the prolapse of the distal portion of the guidewire is corrected at block 820, advancement of the guidewire along the path resumes and the process continues at blocks 804 to track the movement of the device through the path. At block 810, if the remaining path length is equal to zero, the distal portion of the guidewire has reached the target location or point. The movement of the guidewire is stopped and navigation ended at block 812.

Returning to FIG. 4, at block 410 if the target location is reached, e.g., the remaining path length equals zero, navigation of the device is ended at block 412. If the target has not been reached at block 410 then the navigation process continues at block 408.

Computer-executable instructions for navigating a device through a path to a target location and generating a mask of a path to a target location according to the above-described method may be stored on a form of computer readable media. Computer readable media includes volatile and non-volatile, removable, and non-removable media implemented in any method or technology for storage of information such as computer readable instructions, data structures, program modules or other data. Computer readable media includes, but is not limited to, random access memory (RAM), read-only memory (ROM), electrically erasable programmable ROM (EEPROM), flash memory or other memory technology, compact disk ROM (CD-ROM), digital versatile disks (DVD) or other optical storage, magnetic cassettes, magnetic tape, magnetic disk storage or other magnetic storage devices, or any other medium which can be used to store the desired instructions and which may be accessed by system 10 (shown in FIG. 1), including by internet or other computer network form of access.

This written description used examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims. The order and sequence of any process or method steps may be varied or re-sequenced according to alternative embodiments.

Many other changes and modifications may be made to the present invention without departing from the spirit thereof. The scope of these and other changes will become apparent from the appended claims.

We claim:

1. A method for delivering an elongated medical device along a path to a target location using a catheter procedure system, the method comprising:
   identifying a source point and at least one constraint point;
   calculating the path passing through the source point, the at least one constraint point, and the target location;
   generating a mask of the path;
   determining whether at least one child vessel is connected to the path;
   generating a child vessel mask in response to determining that the at least one child vessel is connected to the path;
   displaying the mask and the child vessel mask on an image associated with the mask;
   tracking a position of a distal portion of the elongated medical device based on a set of real-time images;
   determining a remaining path length based at least on the position of the distal portion of the elongated medical device, the remaining path length being a distance between the distal portion of the elongated medical device and the target location, wherein the remaining path length decreases as the distal portion of the elongated medical device approaches the target location;
   updating the remaining path length during movement of the elongated medical device;
   determining whether the distal portion of the elongated medical device is off path;
   adjusting the position of the elongated medical device in response to the distal portion of the elongated medical device being off path;
   advancing the elongated medical device to the target location at a velocity; and
   adjusting the velocity based on the remaining path length, the velocity being proportional to the remaining path length.

2. The method according to claim 1, wherein the generating a mask of the path includes generating a mask for each phase of a physiological cycle.

3. The method according to claim 2, further comprising displaying each mask on an image corresponding to the phase of a heart cycle associated with the mask.

4. The method according to claim 1, wherein the determining whether the distal portion of the elongated medical device is off path is based on the remaining path length.

5. The method according to claim 4, wherein the adjusting the position of the elongated medical device includes adjusting the position of the elongated medical device in response to the remaining path length being a negative number.

6. The method according to claim 1, wherein the adjusting the position of the elongated medical device comprises retracting the elongated medical device.

7. The method according to claim 1, wherein the adjusting the position of the elongated medical device comprises rotating and retracting the elongated medical device.

8. The method according to claim 1, wherein the elongated medical device is a guidewire.

9. The method according to claim 1, wherein the image on which the mask is displayed is a fixed reference image of a region of interest.

10. The method according to claim 1, wherein the image on which the mask is displayed is a real-time image of a region of interest.

11. The method according to claim 1, wherein the set of real-time images are fluoroscopic images.

12. The method according to claim 1, further comprising generating a mask of a set of branches connected to the path and displaying the mask for the set of branches on an image associated with the mask.

13. The method according to claim 12, wherein the generating a mask of a set of branches includes generating a mask for each phase of a physiological cycle.

14. The method according to claim 5, wherein the remaining path length transitions to a negative number when the distal portion of the elongated medical device travels into a branch.

15. The method according to claim 5, wherein the remaining path length transitions to a negative number when the distal portion of the elongated medical device travels past the target location.

16. The method according to claim 1, wherein the remaining path length is equal to zero when the distal portion of the elongated medical device reaches the target location.

17. The method according to claim 1, further comprising generating an alert in response to the distal position of the elongated medical device being off path.

18. A system for delivering an elongated medical device along a path to a target location, the system comprising:
an imaging system; and
a catheter procedure system coupled to the imaging system, the catheter procedure system including
a bedside system including an elongated medical device and a drive assembly configured to drive the elongated medical device, and
a workstation coupled to the bedside system, the workstation including
a user interface,
a display, and
a controller coupled to the bedside system, the user interface and the imaging system, the controller programmed to
identify a source point and at least one constraint point,
calculate the path passing through the source point, the at lest one constraint point, and the target location,
generate a mask of the path,
determine whether at least one child vessel is connected to the path,
generate a child vessel mask in response to determining that the at least one child vessel is connected to the path,
displaying the mask and the child vessel mask on an image associated with the mask on the display,
track a position of a distal portion of the elongated medical device based on a set of real-time images acquired by the imaging system,
determine a remaining path length based at least on the position of the distal portion of the elongated medical device, the remaining path length being a distance between the distal portion of the elongated medical device and the target location, wherein the remaining path length decreases as the distal portion of the elongated medical device approaches the target location,
update the remaining path length during movement of the elongated medical device,
determine whether the distal portion of the elongated medical device is off path,
adjust the position of the distal portion of the elongated medical device in response to the distal portion of the elongated medical device being off path,
advance the elongated medical device to the target location at a velocity, and
adjust the velocity based on the remaining path length, the velocity being proportional to the remaining path length.

19. The system according to claim 18, wherein the controller is further programmed to generate a mask for each phase of a physiological cycle.

20. The system according to claim 19, wherein the workstation further comprises a display and wherein the controller is further programmed to display each mask on an image corresponding to the phase of a heart cycle associated with the mask on the display.

21. The system according to claim 18, wherein the controller is programmed to determine whether the distal portion of the elongated medical device is off path is based on the remaining path length.

22. The system according to claim 21, wherein the controller is programmed to adjust the position of the distal portion of the elongated medical device in response to the remaining path length being a negative number.

23. The system according to claim 18, wherein the position of the distal portion of the elongated medical device is adjusted by retracting the elongated medical device using the drive assembly.

24. The system according to claim 18, wherein the position of the distal portion of the elongated medical device is adjusted by rotating and retracting the elongated medical device using the drive assembly.

25. The system according to claim 18, wherein the elongated medical device is a guidewire.

26. The system according to claim 25, wherein a tip of the guidewire is radiopaque.

27. The system according to claim 18, wherein the image on which the mask is displayed is a fixed reference image of a region of interest.

28. The system according to claim 18, wherein the image on which the mask is displayed is a real-time image of a region of interest.

29. The system according to claim 18, wherein the imaging system is a fluoroscopy system.

30. The system according to claim 29, wherein the set of real-time images are fluoroscopic images.

31. The system according to claim 18, wherein the controller is further programmed to adjust the position of the distal portion of the elongated medical device in response to detecting a prolapse.

32. The system according to claim 18, wherein the workstation comprises a display and wherein the controller is programmed to generate a mask of a set of branches connected to the path and display each mask for the set of branches on an image associated with the mask on the display.

33. The system according to claim 32, wherein the controller is programmed to generate a mask of a set of branches includes generating a mask for each phase of a physiological cycle.

34. The system according to claim 22, wherein the remaining path length transitions to a negative number when the distal portion of the elongated medical device travels into a branch.

35. The system according to claim 22, wherein the remaining path length transitions to a negative number when the distal portion of the elongated medical device travels past the target location.

36. The system according to claim 18, wherein the remaining path length is equal to zero when the distal portion of the elongated medical device reaches the target location.

37. The system according to claim 21, wherein the controller is further programmed to generate an alert in response to the remaining path length being a negative number.

38. The method according to claim 1, further comprising monitoring the distal portion of the elongated medical device in the set of real-time images to identify a prolapse.

39. The system according to claim 18, wherein the controller is further programmed to monitor the distal portion of the elongated medical device in the set of real-time images to identify a prolapse.

40. The method according to claim 1, wherein the velocity decreases as the remaining path length decreases.

41. The method according to claim 1, wherein the mask and the child vessel mask are displayed using different colors.

42. The method according to claim 1, wherein the mask and the child vessel mask are generated for each phase of a physiological cycle.

43. The method according to claim 1, further comprising:
  displaying the remaining path length on a display including the image; and
  wherein the remaining path length is displayed in pixels.

44. The method according to claim 38, further comprising adjusting the position of the elongated medical device in response to detecting a prolapse.

45. The method according to claim 38, further comprising generating an alert in response to detecting a prolapse.

46. The system according to claim 39, wherein the controller is further programmed to generate an alert in response to detecting a prolapse.

* * * * *